US010617321B2

(12) United States Patent
Slater et al.

(10) Patent No.: US 10,617,321 B2
(45) Date of Patent: Apr. 14, 2020

(54) METHODS AND SYSTEMS FOR FOOD ORDERING

(71) Applicant: Walmart Apollo, LLC, Bentonville, AR (US)

(72) Inventors: Kenneth Slater, Oswaldtwistle (GB); Christi J. Odell, Bentonville, AR (US); Robert L. McKeel, Rogers, AR (US); Paul Morley, Hambleton (GB); Todd D. Mattingly, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 132 days.

(21) Appl. No.: 15/586,545

(22) Filed: May 4, 2017

(65) Prior Publication Data

US 2017/0323375 A1 Nov. 9, 2017

Related U.S. Application Data

(60) Provisional application No. 62/332,289, filed on May 5, 2016.

(51) Int. Cl.
*G06Q 30/00* (2012.01)
*A61B 5/0484* (2006.01)
(Continued)

(52) U.S. Cl.
CPC .......... *A61B 5/0484* (2013.01); *A61B 5/4076* (2013.01); *A61B 5/6814* (2013.01);
(Continued)

(58) Field of Classification Search
CPC .. G06Q 30/06; G06Q 20/085; G06Q 30/0643; G06Q 30/0621; G06Q 30/0619;
(Continued)

(56) References Cited

U.S. PATENT DOCUMENTS 7,974,873 B2 * 7/2011 Simmons ......... G06Q 10/06313
705/7.29
9,129,289 B2 9/2015 Vaughn
(Continued)

OTHER PUBLICATIONS

"IRMA: Supply Chain Management of Growing Importance," Jaffee, Larry. Medialine 10.01: 26. Future Publishing Ltd. (Jan. 2005); Dialog #200017113; 5pgs. (Year: 2005).*
(Continued)

*Primary Examiner* — Robert M Pond
(74) *Attorney, Agent, or Firm* — Fitch, Even, Tabin & Flannery LLP

(57) ABSTRACT

In some embodiments, apparatuses and methods are provided herein useful to receive, facilitate, and manage food ordering, especially remote, electronic food ordering. In some embodiments, a food order processing and management system includes an electronic user interface that receives a food order, a database with a plurality of food preparation facilities and capabilities associated therewith, and a central computer coupled to the database, where the central computer is configured to maintain the capabilities of the various food preparation facilities, such as the available ingredients and preparation selections in the database, receive a retrieval time for a particular food preparation facility and present the available capabilities to the user based on the updated database, and notify the food preparation facility of the details of the food order including the selected ingredients and preparation details, along with the retrieval time.

24 Claims, 13 Drawing Sheets

(51) Int. Cl.
*G06F 16/9535* (2019.01)
*G06Q 30/06* (2012.01)
*G06Q 20/08* (2012.01)
*A61B 5/00* (2006.01)

(52) U.S. Cl.
CPC ........ *A61B 5/7225* (2013.01); *G06F 16/9535* (2019.01); *G06Q 20/085* (2013.01); *G06Q 30/0619* (2013.01); *G06Q 30/0621* (2013.01); *G06Q 30/0643* (2013.01); *A61B 2562/164* (2013.01)

(58) Field of Classification Search
CPC . G06F 16/9535; A61B 5/0484; A61B 5/4076; A61B 5/6814; A61B 5/7225
USPC ...................................................... 705/26, 27
See application file for complete search history.

(56) References Cited

U.S. PATENT DOCUMENTS

| | | | | |
|---|---|---|---|---|
| 2002/0188495 | A1* | 12/2002 | Banerjee | G06Q 10/087 705/15 |
| 2005/0049922 | A1 | 3/2005 | Kargman | |
| 2008/0124434 | A1* | 5/2008 | Hrudka | G06Q 10/087 426/233 |
| 2009/0228325 | A1* | 9/2009 | Simmons | G06Q 10/06313 705/7.23 |
| 2011/0258058 | A1 | 10/2011 | Carroll | |
| 2013/0317921 | A1 | 11/2013 | Havas | |
| 2014/0058902 | A1 | 2/2014 | Taylor | |
| 2014/0136366 | A1 | 5/2014 | Carroll | |
| 2014/0214465 | A1 | 7/2014 | L'Heureux | |
| 2014/0279081 | A1 | 9/2014 | Marx | |
| 2014/0324607 | A1 | 10/2014 | Frehn | |
| 2014/0330740 | A1 | 11/2014 | Hoffmann | |
| 2015/0019354 | A1 | 1/2015 | Chan | |

OTHER PUBLICATIONS

"Fast Food Gets Personal: The future of burger joints and smoothie bars involves customer-friendly technologies that will make fast food more of a service and less of a destination," Nash, Kim S. CIO 26.9: n/a. CXO Media, Inc. (Apr. 1, 2013); Dialog #1367539236; 9pgs. (Year: 2013).*

Papa Johns; "Terms & Conditions—Order Quality Pizza Online With Papa Johns;" http://www.papajohns.co.uk/terms-and-conditions.aspx; accessed Jan. 19, 2016; pp. 1-8.

PCT App. No. PCT/US2017/031267; International Search Report and Written Opinion dated Jul. 21, 2017; pp. 1-14.

* cited by examiner

METHODS AND SYSTEMS FOR FOOD ORDERING

CROSS-REFERENCE TO RELATED APPLICATION

This application claims the benefit of U.S. Provisional Application No. 62/332,289, filed May 5, 2016, which is incorporated herein by reference in its entirety.

TECHNICAL FIELD

This invention relates generally to receiving and managing food orders.

BACKGROUND

Many retail food locations, such as restaurants and grocery stores, permit customers to place orders for prepared food items for pickup or retrieval at the retail food location. Further, some of these establishments allow customers to place their orders for pickup prior to arrival at the retail location, such as by submitting the order over the phone or via the Internet. Many customers also prefer their food orders to be prepared in a customized manner or in a certain time frame prior to pickup to ensure freshness.

In addition to the convenience that retail food locations aim to provide customers, the retail food locations are interested in managing the provision of the food orders in a reliable and consistent manner to ensure a positive customer experience. Accordingly, it can be advantageous to improve the customers' ordering experience and the retail food location's management of the food orders.

BRIEF DESCRIPTION OF THE DRAWINGS

Disclosed herein are embodiments of systems, apparatuses and methods pertaining to a method and system for food ordering. This description includes drawings, wherein.

Figure 1:
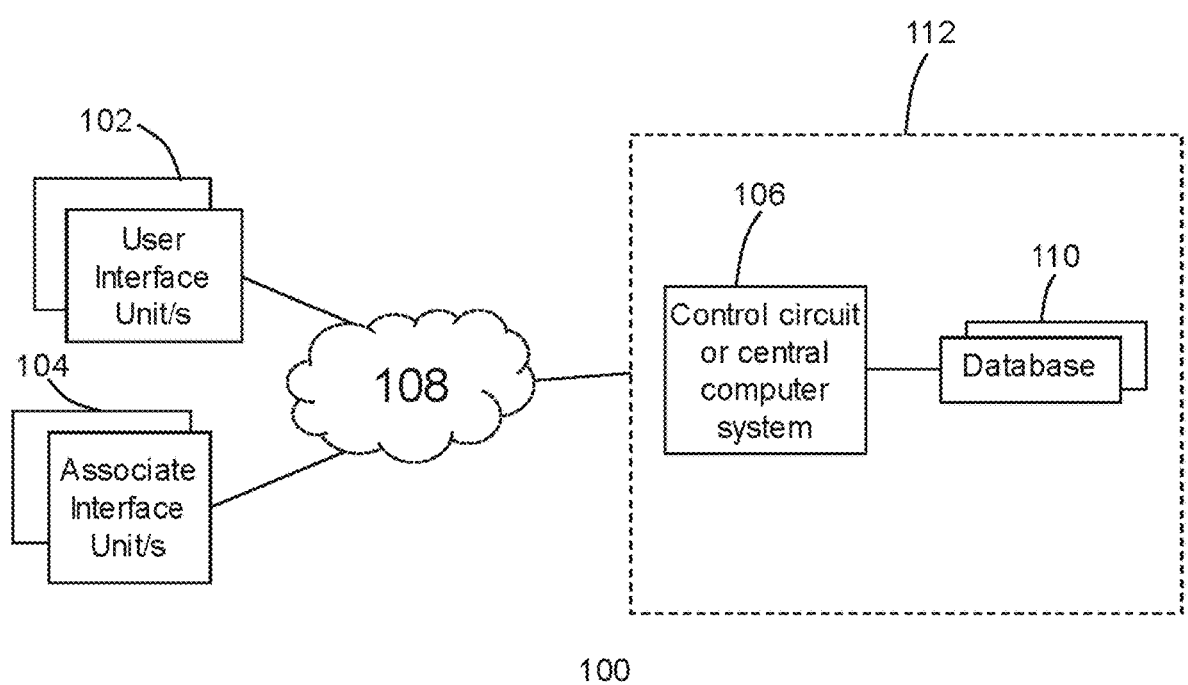
FIG. 1 illustrates a simplified block diagram in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein useful to a food order processing and management system facilitating electronic food order placement based on a food preparation facility's currently available selections. In some embodiments, the food order processing and management system includes an electronic user interface unit that receives a food order, a database of food preparation facilities and capabilities associated with each of the preparation facilities, and a control circuit or central computer coupled to the database and in communication with the user interface. The central computer maintains, in the database, the capabilities associated with each of the plurality of food preparation facilities including ingredient and food preparation selections available for selection and receives a user-selected retrieval time and a user-selected food preparation facility for the food order received at the user interface unit. Further, the central computer presents, based on the information from the database, the available ingredients and food preparation selections to the user based on the received user-selected retrieval time and the user-selected food preparation facility and subsequently receives ingredient and food preparation selections from the user. Then, the central computer notifies the user-selected food preparation facility of the details of the food order including the retrieval time and the ingredient and food preparation selections.

The central computer system updates the currently available ingredients and food preparation selections substantially in real-time. To that end, the central computer may receive information about available selections from associate interfaces at the various food preparation facilities.

In one aspect, each of the food preparation facilities displays or presents a plurality of received food orders to associates responsible for preparing the food orders. Accordingly, in one illustrative embodiment, the food preparation facilities may have one or more associate interfaces disposed therein. Thus, an associate in the food preparation facility can view, via the associate interface, the submitted food orders and subsequently prepare the food orders for retrieval or pickup before the selected retrieval time.

As suggested above, the central computer receives, via the user interface, a retrieval time for a selected food preparation facility. In one illustrative approach, the central computer system is configured to modify the user-selected retrieval time of the food order if the selected food preparation facility cannot accommodate the food order having the received ingredient and food preparation selections made by the user. In yet another approach, the central computer system notifies the user that the selected food preparation facility cannot accommodate the user-selected retrieval time of the food order based on the received ingredient and food preparation selections made by the user. In such a circumstance, the user may be provided an opportunity to select an alternative retrieval time, to select another food preparation facility, or to cancel the food order.

To maintain a quick and easy food ordering experience, the user interface may not require payment for the food order at the time of order submission. In this manner, the user may quickly and easily submit a desired food order without the time or financial commitment often attendance electronic food order submission. Accordingly, the food preparation facilities are configured to receive payment at the time of order retrieval.

A number of users may not retrieve their food orders because no payment was required for the order prior to preparation of the food. In one illustrative embodiment, if the user or customer has not retrieved the food order within a predetermined amount of time after the user-selected retrieval time, the food preparation facility can provide the food order for purchase or consumption to other individuals.

In another illustrative aspect, customers are able to order customized food items according to a method described herein including, for example, presenting an opportunity to initiate a food order, receiving a retrieval time and a selected food preparation facility for the food order from an electronic user device, and presenting available food items for customization including ingredients and food preparation offerings associated with the selected food preparation facility based on information in the database, and receiving the food order with a customized food item. By one approach, the method further includes maintaining, in the database, capabilities associated with each of a plurality of food preparation facilities. Upon receipt of the selected food preparation facility and retrieval time, the method, pursuant to one illustrative embodiment, determines whether the selected food preparation facility can accommodate the food order and the retrieval time and notifies the selected food preparation facility of the retrieval time and the food order with the customized food item(s). By one approach, once the customer arrives at the food preparation facility to retrieve the food order, the facility receives payment for the food order when the user retrieves the food order at the selected food preparation facility.

FIG. 1 illustrates a simplified block diagram of an exemplary food ordering system 100, according to some embodiments, which facilitates receiving, processing, and managing food orders for a plurality of retail food preparation facilities such as grocery stores, restaurants, and the like. The system 100 includes electronic user interface unit(s) 102, a control circuit or central computer 106, and a database 110 of a plurality of food preparation facilities and their available selections. While the central computer system 106 and database 110 are illustrated as separate entities within the control system 112 in FIG. 1, it should be understood that the control system 112 may include both integrated and separate components. In addition, the system 100 may include associate interface unit(s) 104 at the food preparation facilities. As illustrated, the interface units 102, 104 may be communicatively coupled over one or more distributed communication networks 108 with the central computer system or control circuit 106, directly or indirectly, such as through a network 108 (e.g., LAN, WAN, Internet, cellular, Wi-Fi, other such communication networks or combination of two or more of such networks).

The electronic user interface unit(s) 102 are configured to receive a food order from a user and may be located remotely from the food preparation facility. By another approach, the electronic user interface unit(s) 102 include some remotely located units and some units located at the food preparation facility. In one illustrative embodiment, the electronic user interface unit(s) 102 include portable and non-portable user interface units (e.g., smart phones, tablets, desktop computers, laptops, optical head-mounted display systems, smart watch systems, shopping facility specific wireless communication devices, kiosk devices, scanning devices, and other such devices). In one illustrative embodiment, the electronic user interface 102 has a display that can provide information to and receive information from the user. FIGS. 3-7, discussed below, illustrate examples of screen shots that may be presented on one such display. In one embodiment, after an order is submitted, the central computer system 106 may notify the user, via the electronic user interface unit(s) 102, of the status of the user's order such as, for example, order received, order cooking, order prepared, and order retrieved.

In one illustrative embodiment, the central computer system 106 may suggest optional food preparation facilities for selection by the user. By one approach, the central computer system 106 may suggest a food preparation facility previously visited. By another approach, the central computer system 106 is configured to present the user with suggested food preparation facilities based on a user's location, which may be input into a prompt on the electronic user interface unit 102 or obtained from the user interface unit 102 without requiring user input. By some approaches, the system 106 receives location information through, for example, a software application that may cause the user interface units 102 to communication location information (e.g., global positioning information, antenna information, antenna triangulation information, movement sensor information, and the like).

The system 100 also may include one or more associate interface units 104 that permit the food preparation facilities, in communication with the central computer system 106, to present a plurality of received food orders to associates at the food preparation facilities. By one approach, some of these associate interface units 104 may be configured to receive payment for remotely-placed orders at the food preparation facilities. In yet another approach, the food preparation facilities may include separate registers or point-of-sale terminals to receive payment.

In one embodiment, the associate interface units 104 are configured to receive information regarding available ingredient and food preparation selections from associates at the food preparation facilities. For example, if the oven at a particular food preparation facility breaks, the associate, via the associate interface unit 104, may update the database 110 to indicate that no cooked or baked pizzas are available at that particular food preparation facility. In this way, the database 110, to which the associate interface units 104 are in communication, can be updated substantially in real time.

The control circuit or central computer system 106, which is coupled to the database 110 and in communication with the electronic user interfaces 102 and the associate interfaces 104, maintains the capabilities associated with each of the plurality of food preparation facilities, including available ingredients and food preparation selections available for selection by the user in the database 110. In addition, the database 110 is updated with currently available ingredients and food preparation selections substantially in real time.

In another aspect, the central computer system 106 receives a user-selected retrieval time and a user-selected food preparation facility for the food order at the user interface unit 102. By one approach, if the selected food preparation facility is not able to accommodate the requested retrieval time (such as by not having the ingredient and food preparation selections made by the user), the central computer system 106 modifies the user-selected retrieval time of the food order. For example, if a particular food preparation facility can only bake 10 pizzas in a given hour and other users have already ordered 9 baked pizza from that particular facility, a user cannot obtain 2 baked pizzas from that particular facility at that time. Therefore, the central computer system 106 may modify the user-selected retrieval time to another retrieval time that the food preparation facility can accommodate, such as one that is filled with 9 ordered pizzas. In another aspect, the central computer system 106 may modify the user-selected retrieval time to allow the food preparation facility to accommodate specific food requests. For example, certain thicker crust pizzas may require additional preparation time and the central computer system 106 may modify the user-selected retrieval time if such a pizza is requested. In yet another approach, the central computer system 106 is configured to notify the user that the selected food preparation facility cannot accommodate the user-selected retrieval time of the food order.

In yet another aspect, the central computer system 106 presents the available ingredients and food preparation selections to the user, according to the database 110, based on the user-selected retrieval time and food preparation facility. In this way, a customer will only be presented with the ingredients and options that are currently available. For example, if an associate has updated the database 110, via the associate interface unit 104, to indicate that the oven is broken at a particular food preparation facility, the central computer system 106 will not present the option to order a baked pizza from that particular facility.

Further, by one approach, when the central computer system 106 receives the ingredient and food preparation selections from the user, it notifies the selected food preparation facility of the food order, retrieval time, and the ingredient and food preparation selections. In this manner, the selected food preparation facility is able to prepare the received food order for retrieval at the selected food preparation facility before the selected retrieval time.

In one illustrative example, a customer may seek to place a food order such as a pizza order, and the customer may user their electronic user interface unit 102, such as a mobile computer, to place such a pizza order. The central computer system 106 may maintain the capabilities associate with the pizzeria in the database 110. In this manner, the database may include information regarding available ingredients, such as pizza toppings, crust options, and pizza sizes. The database 110 also may include information regarding the food preparation facility or pizzerias capabilities or available selections, such as whether the facility can prepare uncooked and cooked pizza for retrieval by customers and the number and size of the pizzas available for retrieval. In this manner, the customer can place the pizza order for the desired customized pizza(s) based on the pizza ingredients and preparation selections currently available at their location of choice.

Figure 2:
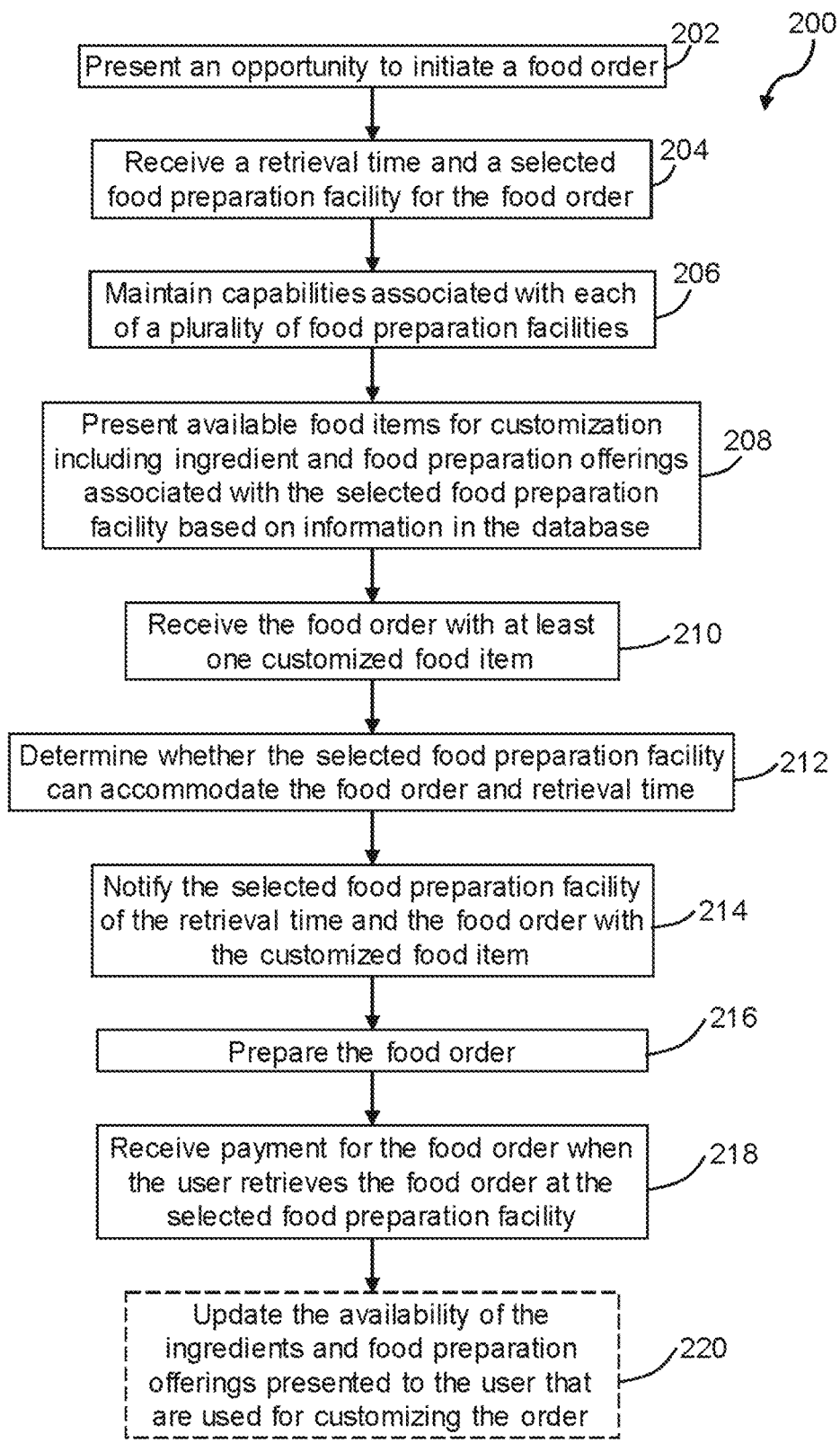
FIG. 2 illustrates a simplified flow diagram in accordance with several embodiments.

Referring now to FIG. 2, a process 200 for receiving, facilitating, and managing food orders according to some embodiments discussed herein is illustrated. The method 200 includes presenting 202 an opportunity to initiate a food order, which may include information regarding the pickup or retrieval time and the restaurant or grocery store location where the user may retrieve the food order. The opportunity may be presented 202 to a user via an electronic user interface unit or device, such as a mobile phone, personal computer, and tablet, among others. Further, by one approach, the user interface may be provided to the electronic user devices by a central computer, such as providing a mobile software application (APP) for download. By another approach, the user interface may be configured to be executed on a device that is in communication with the central computer, such as when a person computer is in communication with the central computer via a network, such as the Internet.

The process 200 also includes receiving 204 a retrieval time and a selected food preparation facility for the food order from the electronic user interface unit or device. In this manner, a user may make a selection at the electronic user interface unit or device and the selection may be transmitted such that it is received by a central computer. By one illustrative approach, the central computer also is configured to modify the retrieval time of a particular food order. For example, the central computer may modify the retrieval time in response to the size of the order being submitted or the type of items being ordered. In another configuration, the central computer may modify the retrieval time based upon circumstances at the selected food preparation facility, such as receipt of additional food orders. Further, the modification may occur while the food order is being initially submitted, such that the user has not finalized the order, or alternatively, the modification may occur subsequent to submission of the food order.

The process 200 includes maintaining 206 a database of capabilities associated with each of the plurality of food preparation facilities from which the users may order. By one approach, the database includes the plurality of ingredients available at each food preparation facilities. For example, the database may include two food preparation facilities and these facilities may have a list of currently available ingredients that includes, for example, tomato sauce, olive oil, chili oil, mozzarella cheese, peperoni, ham, bacon, salami, tuna, olives, green pepper, onion, pineapple, whole wheat crust, thin crust, and thick crust. By another approach, the database includes the available food preparation offerings and capabilities of particular food preparation facilities. For example, the database may include, for example, information on the number of pizzas a particular food preparation facility can prepare in a given time frame and equipment capabilities such as, for example, whether the facility has an oven to bake pizza. Further, the database may have information on the size of the oven and what size or diameter pizzas the oven can accommodate and how many pizzas can be baked in a given period of time.

The process 200 also may include updating 220 the database of capabilities associated with each of the plurality of food preparation facilities. For example, if the first food preparation facility runs out of green pepper, onion, and ham and the second food preparation facility acquires sausage, the database may be updated to reflect the current availability of ingredients at the food preparation facilities. Specifically, the first food preparation facility will be updated in the database to indicate that green peppers, onions, and ham are not available and the second food preparation facility will be updated in the database to indicate the availability of sausage as a topping. By way of another example, the capabilities also may be updated such as, for example, if the oven at a particular food preparation facility is no longer operable, the database can be updated to reflect that baked pizzas are not currently available. In this manner, the customers ordering pizza will have confidence that the particular pizza ordered will be available for pickup because the database can be updated substantially in real time by associates at the food preparation facilities.

In step 208, available food items for customization are presented to a user. The available food items for customization may include the currently available ingredients and food preparation offerings associated with a user's selected food preparation facility based on information in the database. By way of example, if a user selects the first food preparation facility mentioned above, the user interface on the user's device will present tomato sauce, olive oil, chili oil, mozzarella cheese, peperoni, bacon, salami, tuna, olives, pineapple, whole wheat crust, thin crust, and thick crust as available ingredients, but no green peppers, onion, or ham. In addition, the user interface will present the available selections, such as, for example, whether a baked pizza can be ordered and the available pizza sizes. In one illustrative approach, the food preparation selections may include a number of pizzas, pizza size, pizza crust type, and a cooked status.

The process 200 also provides for receiving 210, from a user, a food order with at least one customized item. For example, after selecting the second food preparation facility mentioned above and a retrieval time, a user can order a customized pizza with tomato sauce, sausage, onion, and bacon on a thin crust. Further, the order may be submitted because the presented 208 food items included the currently available sausage, as mentioned above.

In step 212, a determination regarding whether the selected food preparation facility can accommodate the food order and retrieval time is made. For example, if, while a food order is being submitted, another very large order is submitted, the determination may indicate that the selected food preparation facility can no longer accommodate the requested time and that a new, later retrieval time needs to be presented to the user.

After the food order is received 210, the process 200 notifies 214 the selected food preparation facility of the retrieval time and the food order with the customized food item. Then, the selected food preparation facility prepares 216 the food order before the user's retrieval time. In addition to assembling the ingredients, the selected food preparation facility may cook the pizza, if such a selection is available and made by the user. To that end, if a hot food item is ordered, the selected food preparation facility ensures that the pizza or other food item is baked or otherwise cooked before the retrieval time and kept warm to ensure freshness of the food order.

As suggested above, the ability to remotely submit a food order provides convenience and time saving for users. To further expedite the process for customers, the electronic device carried by the user may notify the selected food preparation facility of a user's estimated arrival time. By one approach, a device's global positioning system (GPS) may be activated and in communication with the central computer and the selected food preparation facility.

In step 218, payment for the food order is received when the user retrieves the food order at the selected food preparation facility. In this manner, the user does not submit payment for the food order at the time the order is made, and there is no financial commitment from the user until the food order is retrieved. This provides a fairly streamlined ordering process and also does not require a user to pay for a food order if they do not subsequently retrieve the prepared food order.

Further, if the user does not retrieve the order, the selected food preparation facility may provide the food order for purchase or consumption to individuals other than the user at a pre-determined time after the retrieval time. For example, the selected food preparation facility may provide the food order as a sample for consumption to other facility customers or use the food order or a portion thereof as a part of a demonstration. Alternatively, the facility may offer the food order, or a portion of the food order for sale to other customers.

Figure 3:
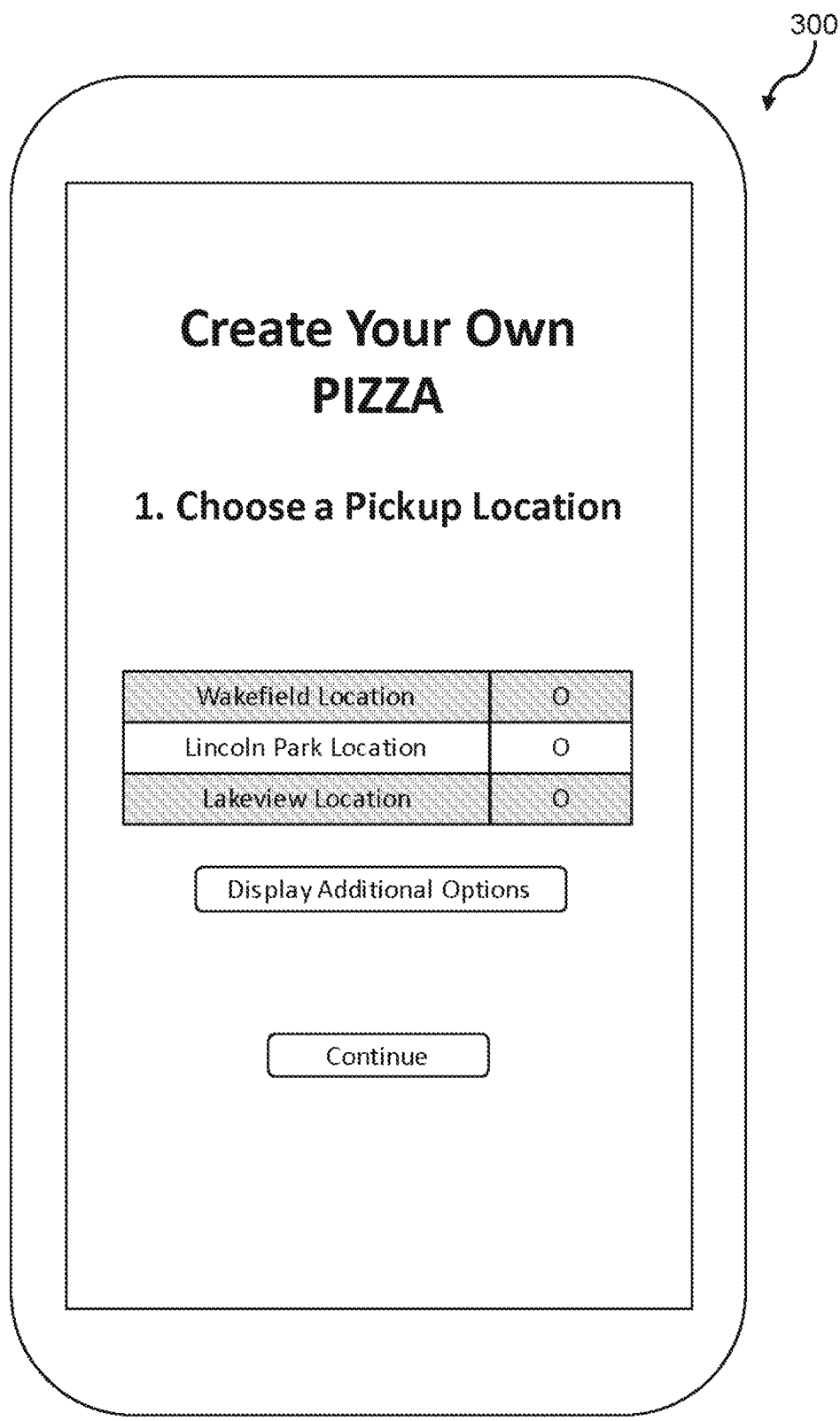
FIGS. 3-7 illustrate simplified screen shots of a user interface unit in accordance with some embodiments.

As suggested above, electronic user devices or units 102 are configured to display a user interface, such as a mobile software application (e.g., an application executed on the unit to display the user interface) or website (e.g., website that provides or serves a user interface to a user device for display on that user device using a browser for example), which conveys and receives information from an end user customer. FIGS. 3-7 illustrate a series of screen shots of an illustrative mobile device with a user interface. The screen shot 300, shown in FIG. 3, illustrates a mobile device providing an opportunity to a user to initiate a food order and select a retrieval location on a mobile device. By one approach, the optional pickup locations listed may be based on information input by the user or the device's location feature, which may provide location details to the mobile software application or website.

Figure 4:
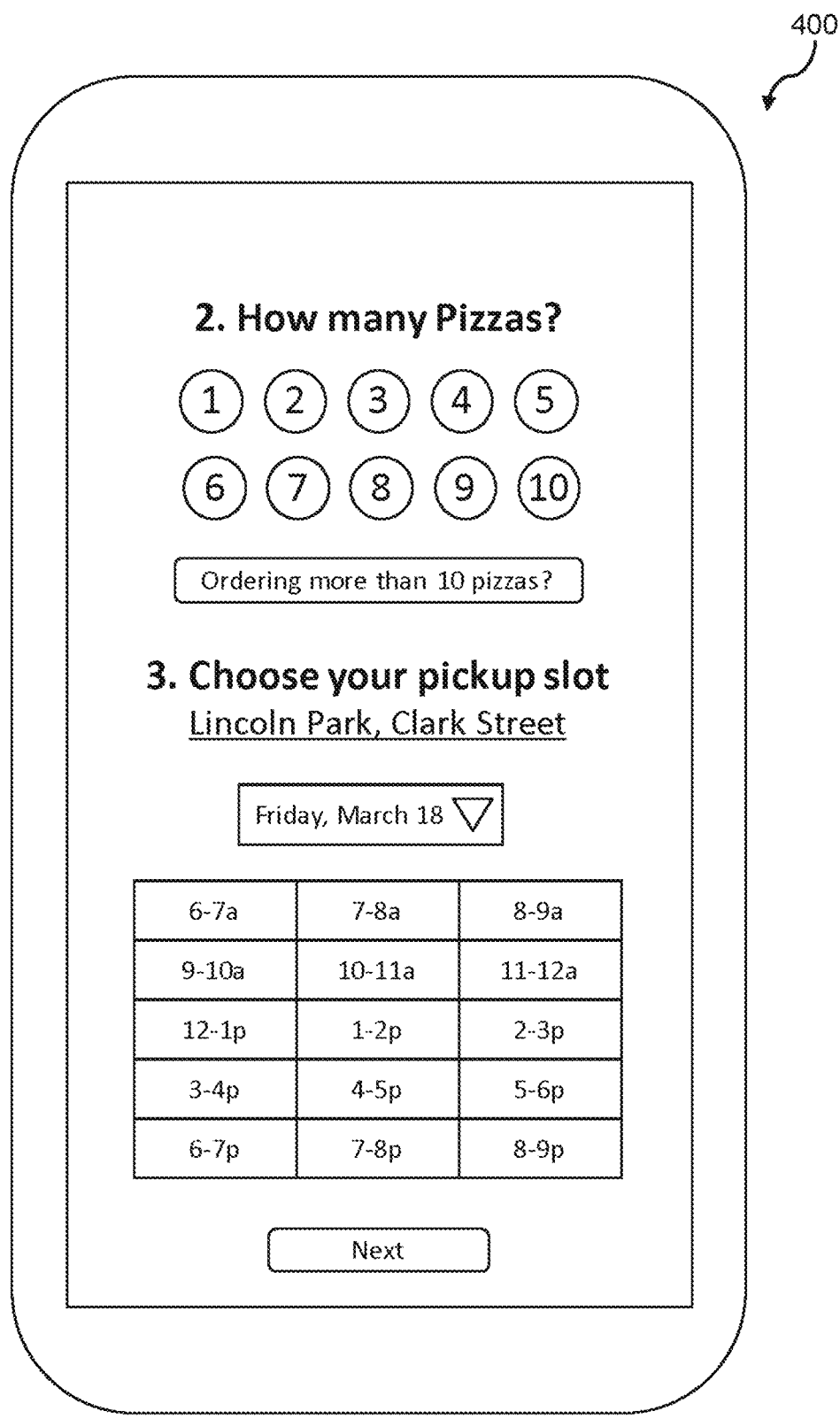
Figure 5:
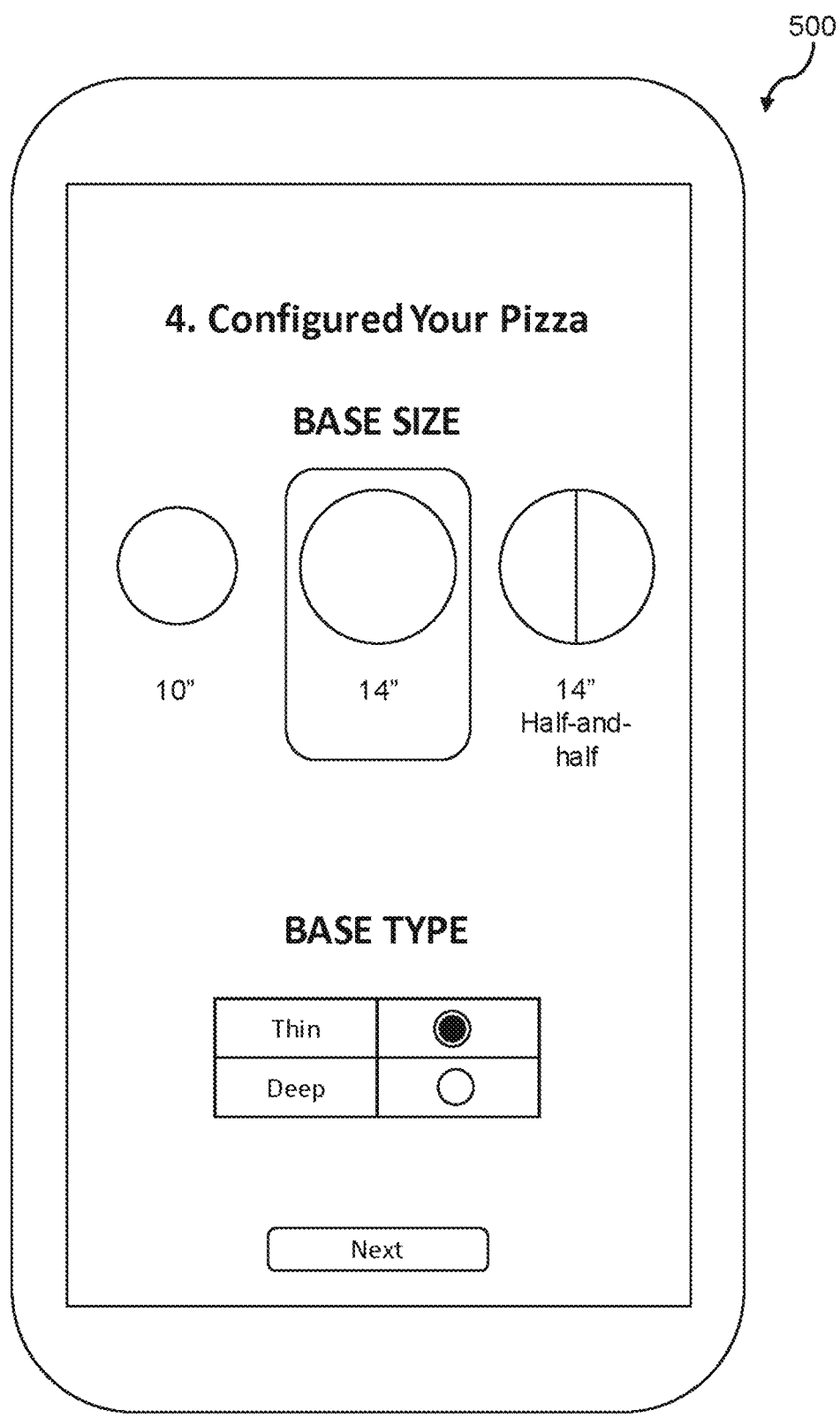
Figure 6:
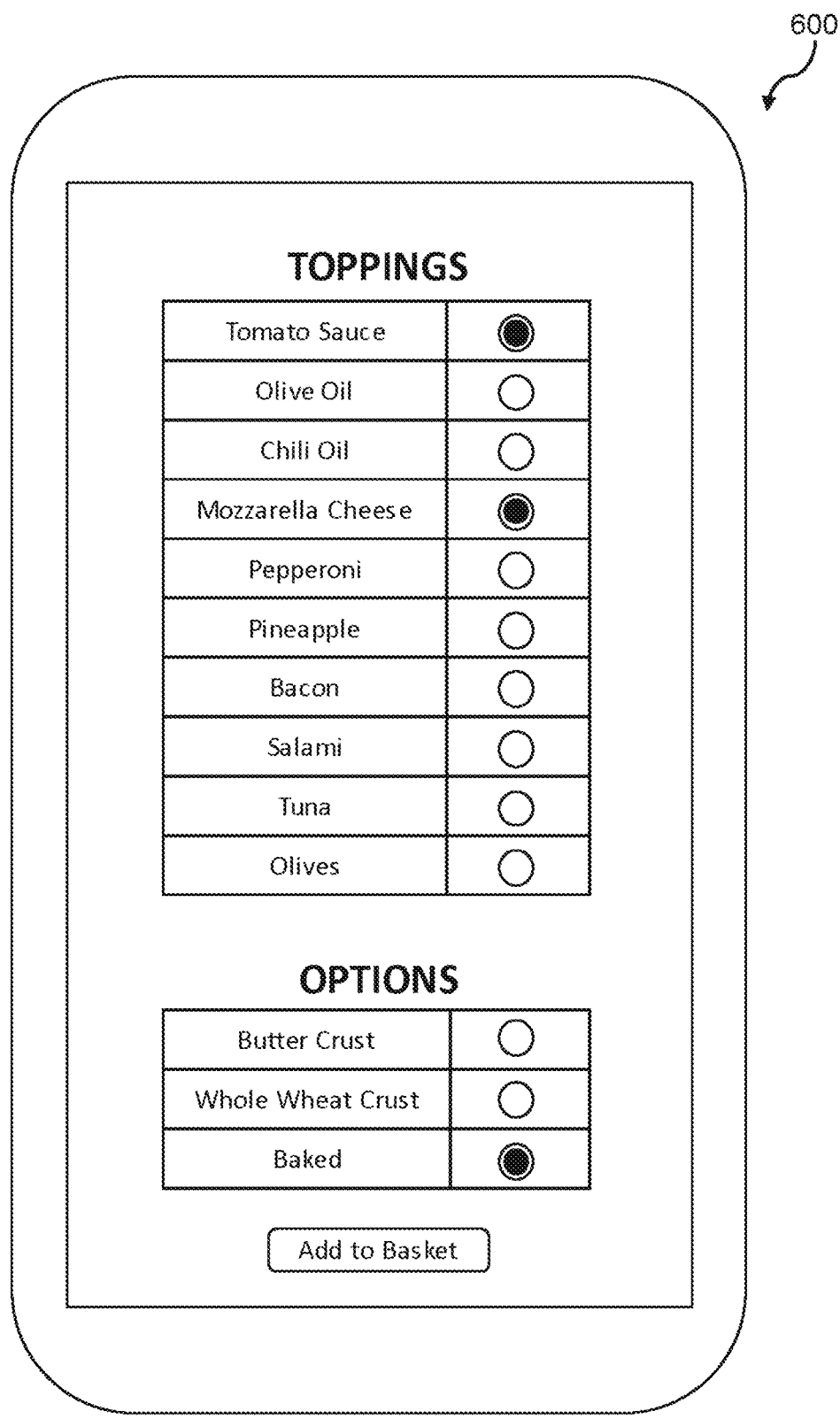
Figure 7:
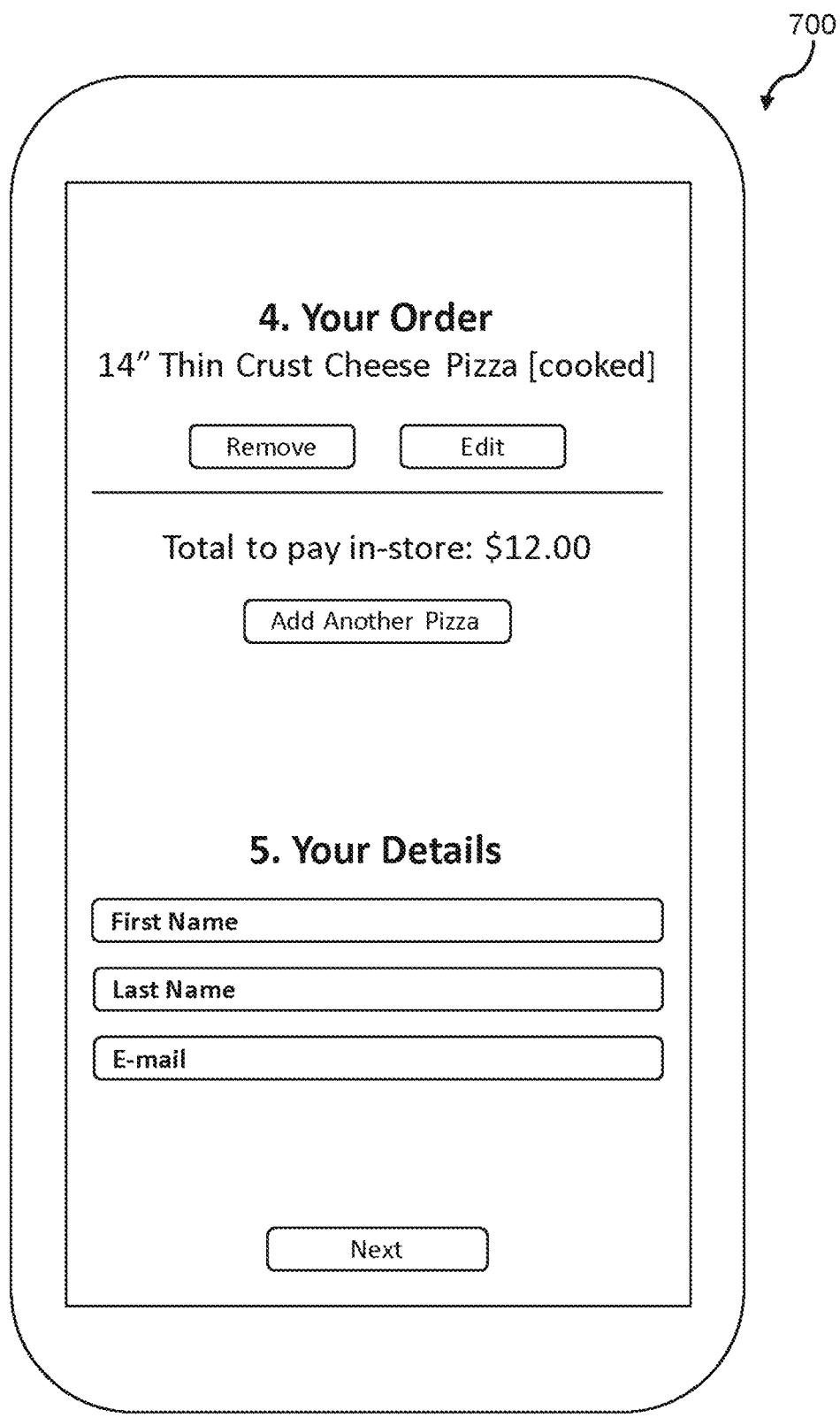

FIG. 4 illustrates a screen shot 400 that provides a user the opportunity to select the amount of food item desired, specifically the number of pizzas, and the retrieval time. Once this information has been entered, the mobile device may present the food items available for customization. A screen shot 500, shown in FIG. 5, illustrates how a customer may select the pizza size and configuration to customize, such as the diameter and the crust type. Once the base pizza configuration has been selected, screen shot 600, shown in FIG. 6 illustrates the toppings and preparation options that the user may select before finalizing the food order. As illustrated in the screen shot 700 of FIG. 7, the user may see a summary of the order and may have an opportunity to modify the order before submitting the order. In addition, the mobile device may notify the user of the total cost of the food order and may request user or customer details, such as, for example, to assist the associate at the food preparation facility in locating the order. Further, the screen shot 700 illustrates how the system may obtain user details associated with the order. In one illustrative example, shown in FIG. 7, the system requests a name and contact information, such as an e-mail address or telephone number. In other configurations, the users may create profiles with a user name and login, which may be used to associate an order with a user.

As mentioned above, the system may present a plurality of food orders to the associate, cook, or server at the food preparation facilities via an associate interface. FIGS. 8-11 show screen shots of an illustrative device with an associate interface configured to assist the associates with management of the food orders. By one approach, the electronic device with the associate interface displays the pizzas or other food items that need to be prepared on a given day and at a given time slot. Further, in one illustrative example, a user can navigate the list, such as by selecting an order to obtain additional details about the order.

Figure 8:
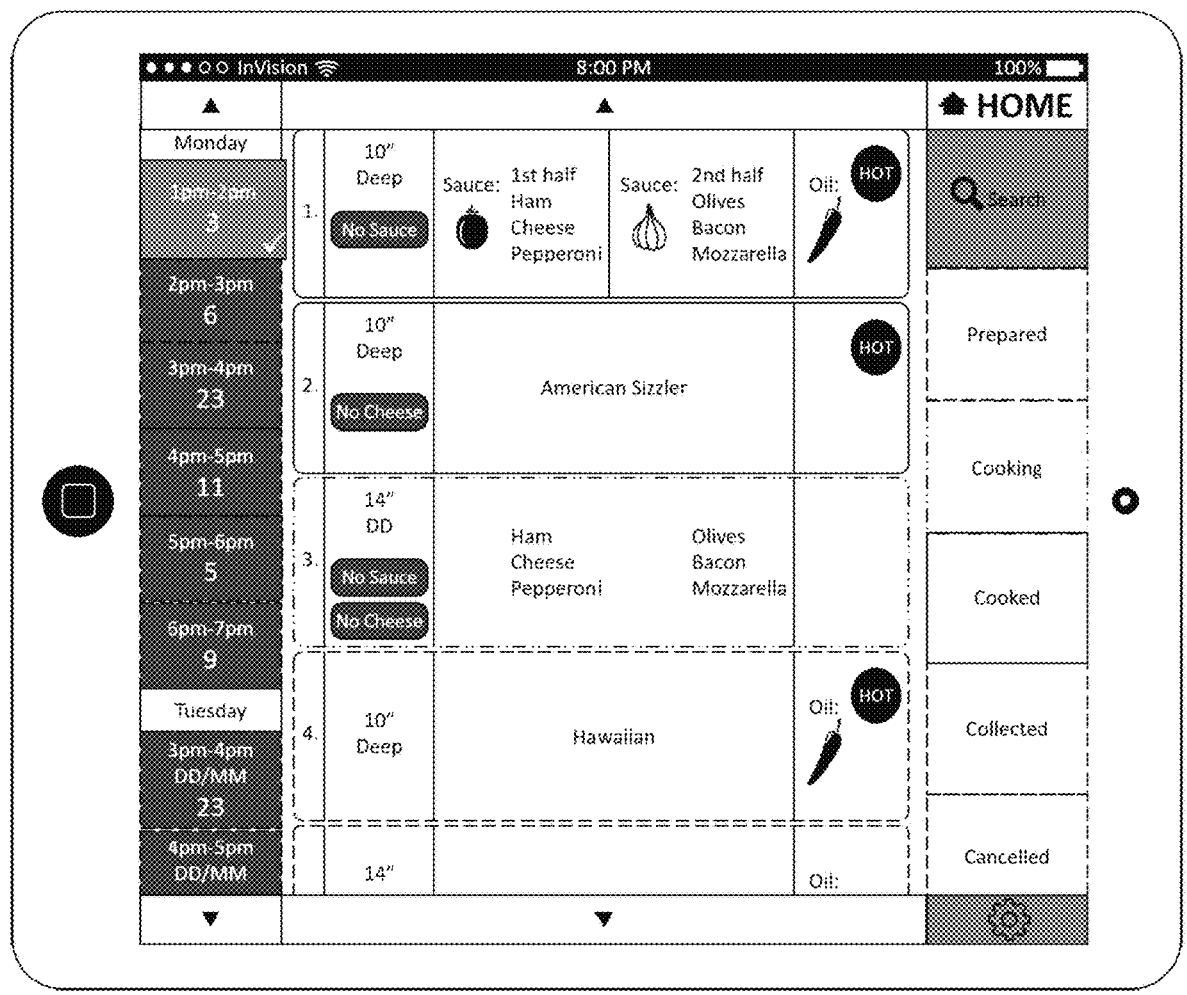
FIGS. 8-11 illustrate simplified screen shots of an associate interface unit in accordance with some embodiments.

For example, FIG. 8 illustrates a screen shot 800 showing four orders that an associate needs to prepare for pickup between 1-2pm on Monday. To further highlight the food orders needing attention, the associate interface may distinguish the food orders requiring immediate attention or action from others. By one approach, a red border is disposed around the orders needing to be prepared immediately in order to satisfy a customer that is scheduled for arrival or pickup with the next 10-15 minutes. By another approach, an amber or yellow border is drawn around orders that need to be prepared within a moderate amount of time, such as within the next 30 minutes. In another aspect, the orders that are not required to be prepared for pickup may be bordered in green. In screen shot 800, the first and second orders are cooked and ready for pickup, as illustrated by the red perimeter of the entries. Both of these orders have a "hot" designation in the right of the order indicating that the pizzas are to be cooked. The third order is has a yellow line drawn around the entry, as illustrated by the dashed line, which indicates that the order needs to be ready within the next 30 minutes. Finally, the fourth order has a green line around the food order, indicating that the order has yet to be prepared. Alternatively, a green designation around the food order may indicate that the order has been prepared and collected by the customer or possibly cancelled by the customer. Once an associate indicates that an order has been completed, the screen shot 900 illustrates how an associate may be provided the opportunity to prepare the next order.

Figure 9:
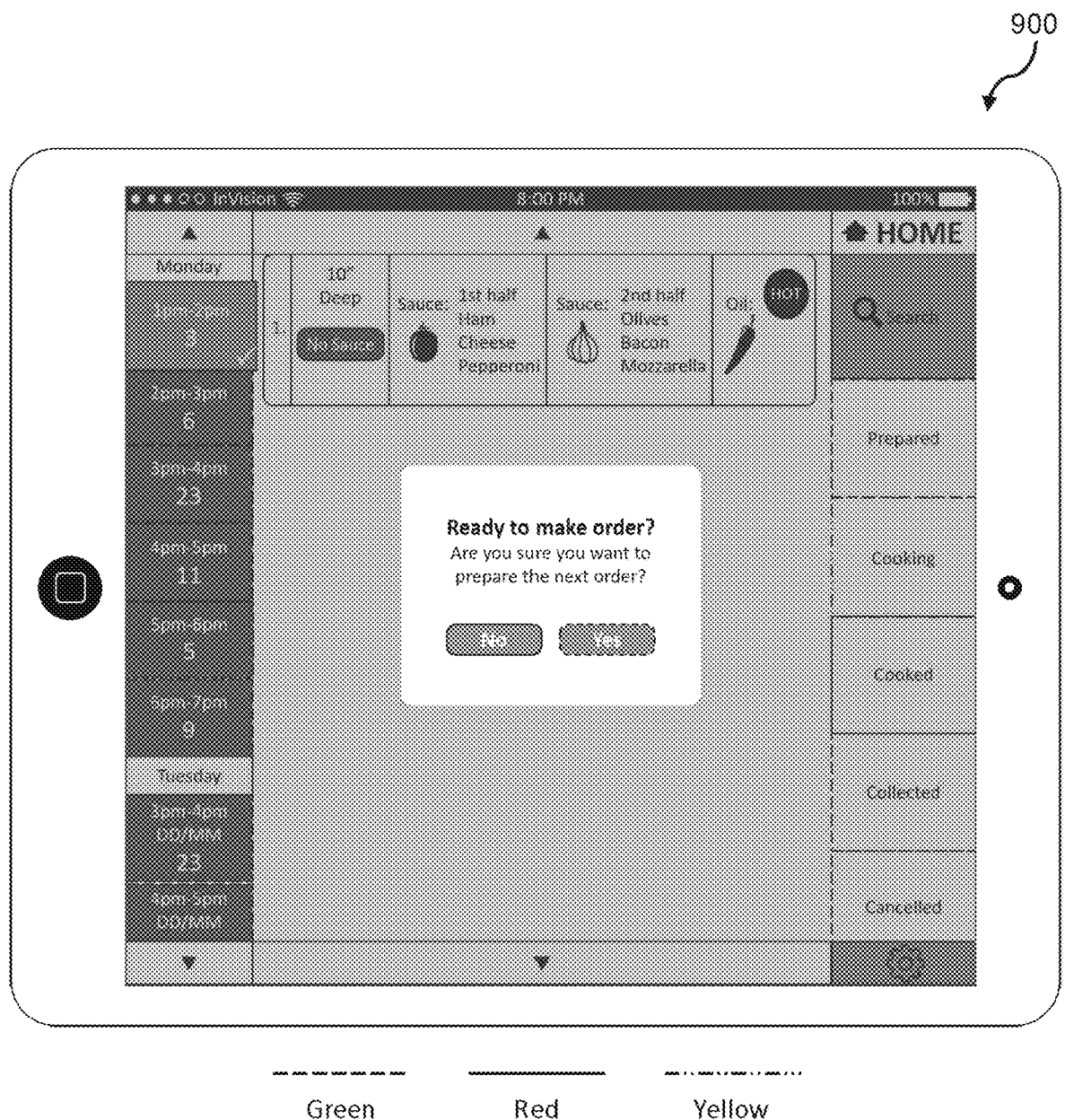
Figure 10:
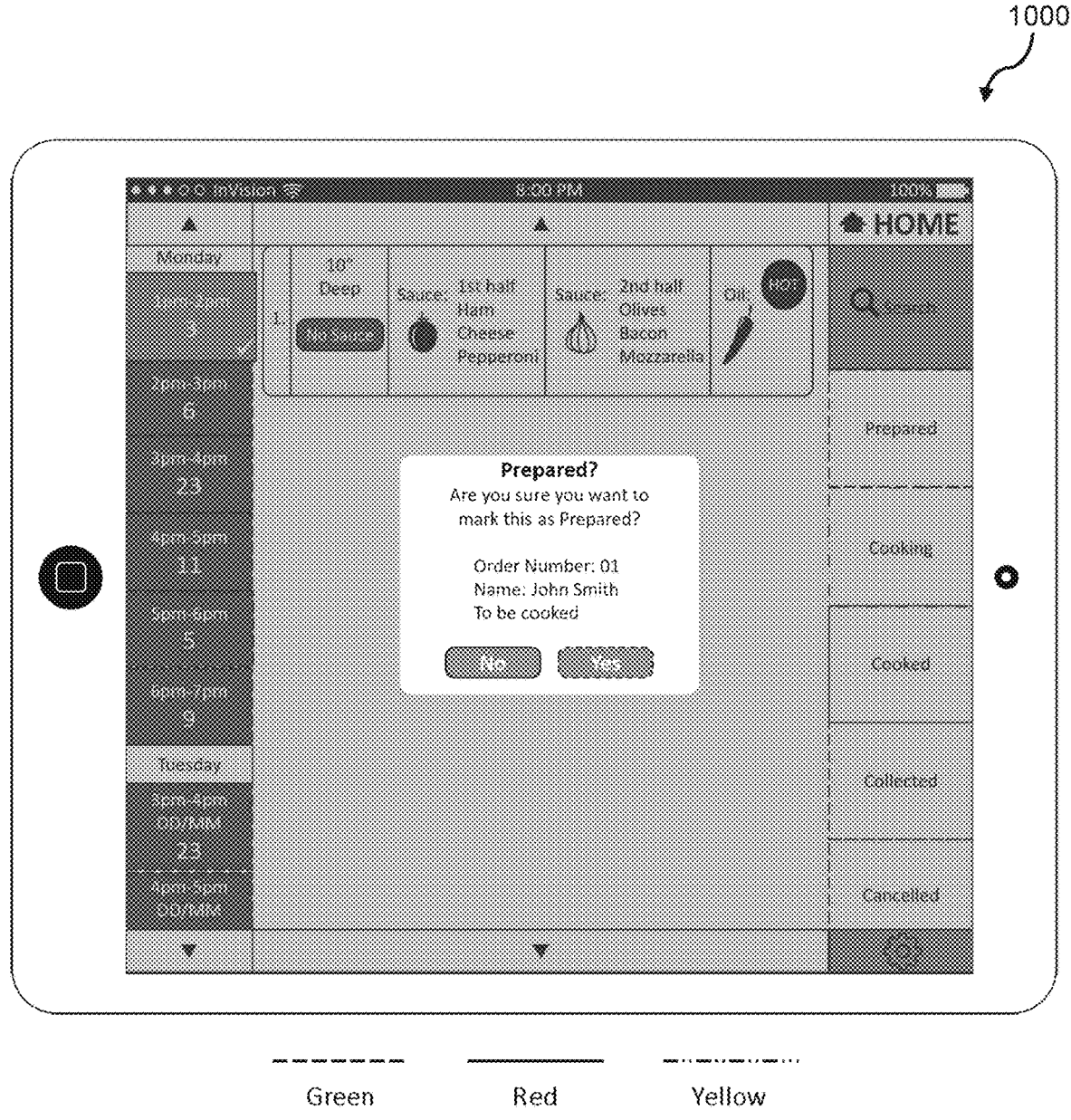

Turning now to FIG. 9, the screen shot 900 of the associate interface illustrates how the system permits the associates to indicate that an order is being made. Further, to indicate that a food order is being prepared, the associate may select the food order in the listing of orders, such as order 01, and then indicate that the associate is going to prepare the order. Accordingly, this updates the list of orders displayed on the associate device to indicate that the order is being prepared. Once the order has been prepared, the associate interface may be updated to indicate that the order has been prepared and is ready for customer pickup. FIG. 10 illustrates screen shot 1000 that provides a prompt to the associate, which confirms whether the food order has been prepared.

The associate interface unit is communicatively coupled to the central computer, which may notify the user of the status of an order. In one embodiment, after the associate has indicated that the order is prepared, the customer may receive an electronic indication (such as a text or SMS notification) that the food order is ready for pickup. In another embodiment, a user may access the central computer to determine the status of an order previously submitted. Further, by having the central computer updated with the status of the order, a user can obtain updated order information substantially in real time.

In one embodiment, the associates are able to review and sort all of the food orders received for a particular food preparation facility. This helps the associate manage the food orders. For example, such visibility with regards to upcoming orders can help associates determine when various ingredients need to be prepared or acquired. By one approach, the associate interface is configured to permit the food orders to be sorted according to retrieval time or the stage or status of an order, such as received, cooking/preparing, prepared, collected, and/or cancelled.

Figure 11:
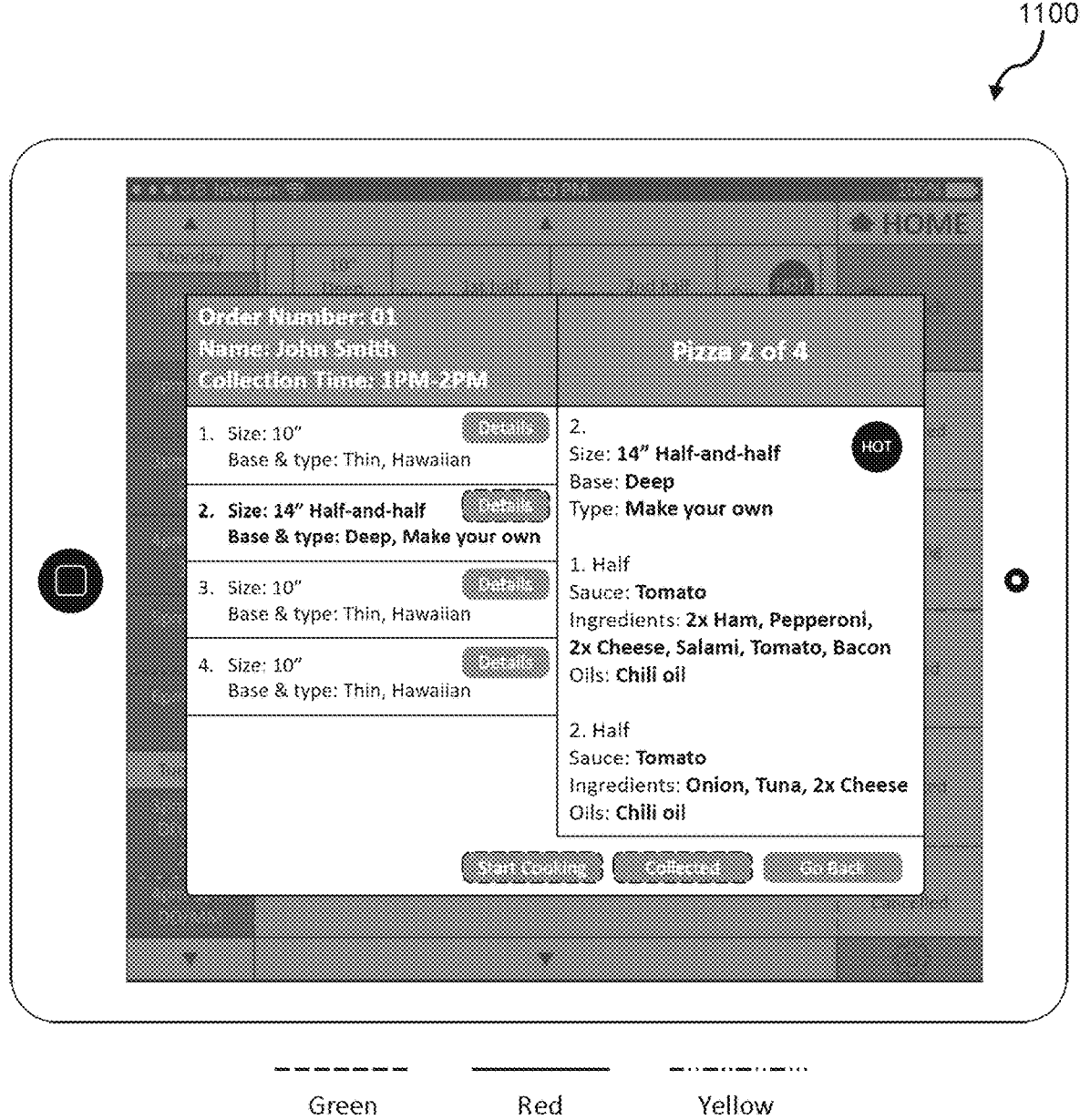

Finally, once a customer or user arrives at the food preparation facility to retrieve the food orders, the associate may select the order on the associate interface and indicate that the order has been retrieved or collected. FIG. 11 illustrates a screen shot 1100 showing one example order summary. Once the customer or user has retrieved or collected the order, the associate may indicate as such in the prompt. As noted above, the user may be able to submit payment for their order at the associate interface unit or at another point of sale terminal. If the associate interface unit is configured to receive payment, the associate interface unit may automatically update the status of the order for which payment has been received by notifying the central computer system and updating the status of the order.

Further, the associate interface also may permit the associate to enter details about the current inventory of the food preparation facility. For example, if the facility is out of green peppers, the associate can enter this information into the associate interface, which can update the database such that this ingredient is no longer presented to customers as an optional ingredient at this particular food preparation facility.

Figure 12:
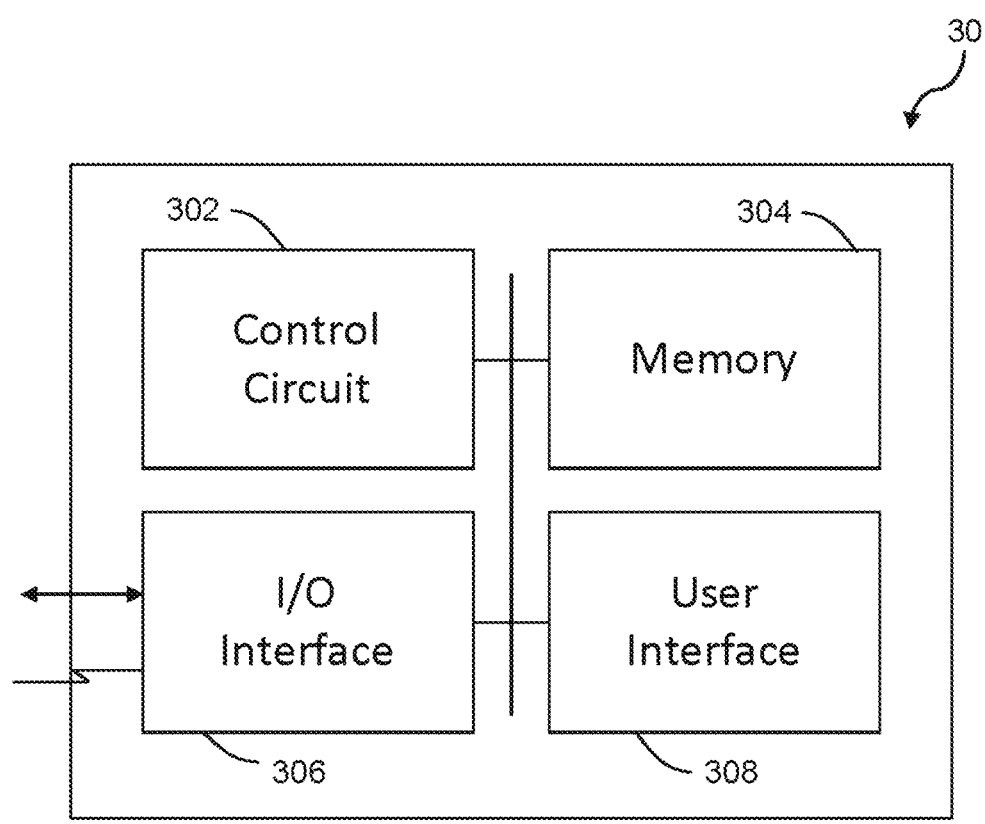
FIG. 12 illustrates an exemplary system for use in implementing systems, apparatuses, devices, methods, techniques, and the like in managing the food ordering system in accordance with some embodiments.

The methods, techniques, systems, devices, services, servers, sources and the like described herein may be utilized, implemented and/or run on many different types of devices and/or systems. Referring to FIG. 12, there is illustrated a system 30 that may be used for any such implementations, in accordance with some embodiments. One or more components of the system 30 may be used to implement any system, apparatus or device mentioned above or below, or parts of such systems, apparatuses or devices, such as for example any of the above or below mentioned food ordering system, user interface units 102, associate interface units 104, and the like. However, the use of the system 30 or any portion thereof is certainly not required.

By way of example, the system 30 may include one or more control circuits 302, memory 304, and input/output (I/O) interfaces and/or devices 306. Some embodiments further include one or more user interfaces 308. The control circuit 302 typically comprises one or more processors and/or microprocessors. The memory 304 stores the operational code or set of instructions that is executed by the control circuit 302 and/or processor to implement the functionality of the food ordering system, database 110, user interface units 102, associate interface units 104 and the like. In some embodiments, the memory 304 also may store some or all of particular data that may be needed to manage food orders, the database, communications described herein and the like. Such data may be pre-stored in the memory, received from an external source, be determined, and/or communicated to the system.

It is understood that the control circuit 302 and/or processor may be implemented as one or more processor devices as are well known in the art. Similarly, the memory 304 may be implemented as one or more memory devices as are well known in the art, such as one or more processor readable and/or computer readable media and can include volatile and/or nonvolatile media, such as RAM, ROM, EEPROM, flash memory and/or other memory technology. Further, the memory 304 is shown as internal to the system 30; however, the memory 304 can be internal, external or a combination of internal and external memory. Additionally, the system typically includes a power supply (not shown), which may be rechargeable, and/or it may receive power from an external source. While FIG. 12 illustrates the various components being coupled together via a bus, it is understood that the various components may actually be coupled to the control circuit 302 and/or one or more other components directly.

Generally, the control circuit 302 and/or electronic components of the system 30 can comprise fixed-purpose hard-wired platforms or can comprise a partially or wholly programmable platform. These architectural options are well known and understood in the art and require no further description here. The system and/or control circuit 302 can be configured (for example, by using corresponding programming as will be well understood by those skilled in the art) to carry out one or more of the steps, actions, and/or functions described herein. In some implementations, the control circuit 302 and the memory 304 may be integrated together, such as in a microcontroller, application specification integrated circuit, field programmable gate array or other such device, or may be separate devices coupled together.

The I/O interface 306 allows wired and/or wireless communication coupling of the system 30 to external components and/or or systems. Typically, the I/O interface 306 provides wired and/or wireless communication (e.g., Wi-Fi, Bluetooth, cellular, RF, and/or other such wireless communication), and may include any known wired and/or wireless interfacing device, circuit and/or connecting device, such as but not limited to one or more transmitter, receiver, transceiver, etc.

The user interface 308 may be used for user input and/or output display. For example, the user interface 308 may include any known input devices, such one or more buttons, knobs, selectors, switches, keys, touch input surfaces, audio input, and/or displays, etc. Additionally, the user interface 308 typically includes one or more output display devices, such as lights, visual indicators, display screens, etc. to convey information to a user or associate, such as, but not limited to food product order(s), location information, pickup time slots, available ingredients and preparation selections, notifications (e.g., text messages, emails, etc.), status information, operating status information, notifications, errors, conditions, and/or other such information. Similarly, the user interface 308 in some embodiments may include audio systems that can receive audio commands or requests verbally issued by a user, and/or output audio content, alerts and the like. Some embodiments may further include one or more location detection systems (e.g., user interface units) that may determine and/or track location information, which may be communicated to one or more other systems (e.g., to the central computer system 106).

In some embodiments, systems, apparatuses and methods are provided to receive, facilitate and manage remote food ordering. In some embodiments, a food order processing system is provided that includes an electronic user interface that may receive a food order, a database with a plurality of food preparation facilities and capabilities associated therewith, and a central computer coupled to the database, where the central computer is configured to maintain the capabilities, such as the available ingredient and preparation selections in the database, receive a retrieval time for a particular food preparation facility, present the available ingredient and preparation selections to the user based on the updated database, and notify the food preparation facility of the details of the food order including the selected ingredients and preparation details, along with the retrieval time.

In some embodiments, the system may include an automated pizza maker. By one approach, the machine is an automated, self-service pizza preparation machine, which operates similarly to a vending machine with capabilities for preparing, and in some configurations, cooking the assembled pizzas. In this manner, the automated pizza preparation machine allows consumers to enjoy customized pizza that is prepared according to their specifications outside of normal business hours, when pizzerias are generally open. Accordingly, such a system may provide consumers with additional pickup or retrieval times (or even locations). The automated pizza maker may be employed with the teachings above regarding ordering of food items via an electronic user interface operable on a mobile device.

Figure 13:
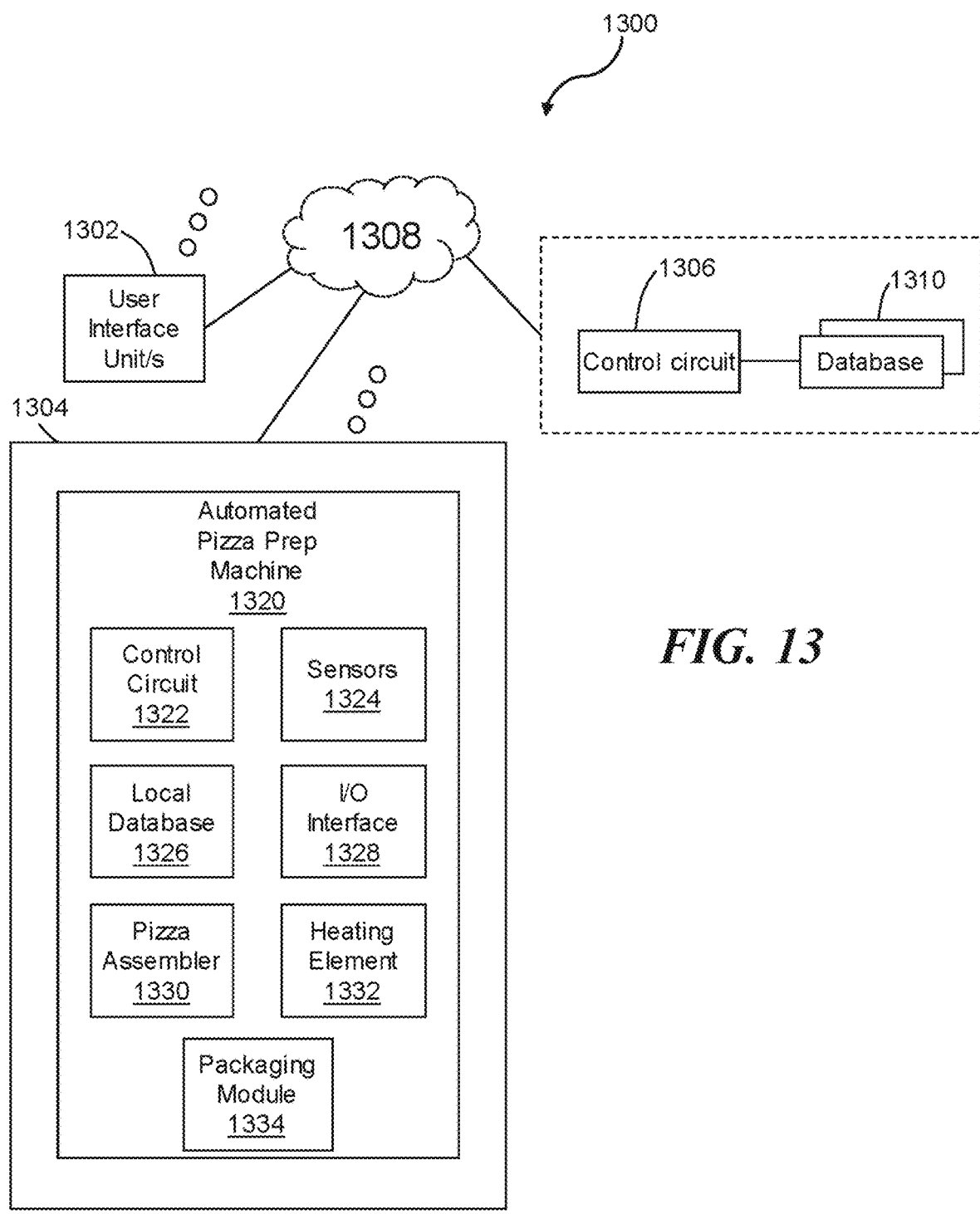
FIG. 13 illustrates a simplified block diagram in accordance with some embodiments.

As illustrated in FIG. 13, by one approach, an automated pizza preparation machine 1320 includes a control circuit 1322 that is in communication with a control circuit 1306 and database 1310 (optionally via network 1308), which may be similar to the control circuit 106, database 110, and network 108 discussed above. The automated pizza preparation machine 1320 may be remotely instructed to prepare (and possibly cook) a pizza such as via the mobile application described above operable on the user interface unit(s) 102, or alternatively, the automated pizza preparation machine 1322 may include an input/output interface 1328 that permits a user to input an order at the machine 1322. In some configurations, the i/o interface 1328 also facilitates retrieval of the prepared pizzas and permits the user to submit payment for pizzas ordered at the machine or remotely.

In one embodiment, the automated pizza preparation machine 1320 includes a control circuit 1322, a local database 1326, sensors 1324, a pizza assembler 1330 *b* (including, for example, a pizza dough or crust dispenser and a topping dispenser), and a cooking or heating element 1332. By one approach, the pizza crust dispenser releases the crusts below the topping dispenser, which can release the toppings directly onto the pizza crust. In some configurations, the user may select, for example, the size of the crust, the amount and type of sauce, cheese, and other toppings, and whether or not the pizza should be heated or cooked. For assembly, preparation, and packaging of the pizza, a variety of different elements, devices, and apparatus may be used, such as, for example, tubes, cylinders, valves, conveyors, robotic arms, motors, racks, levers, platforms, canisters, pumps, and sensors, among others. In addition, portions or sections of the automated pizza preparation machine 1320 will be cooled or employ refrigeration to ensure freshness and safety of the ingredients. In some embodiments, the automated pizza preparation machine 1320 includes a packaging area or module 1334 that permits the machine 1320 to place the pizza in a carton, envelope, box, bag, or other package before dispensing the pizza for receipt by the customer or user. Examples of automated pizza makers (without the remote ordering systems described herein) are found, for example in U.S. Pat. No. 5,997,924 and U.S. Publication Nos. 2011/0059209 and 2011/0209661, all of which are incorporated herein by reference.

The automated pizza preparation machine 1320 may be a self-contained and self-service. Further, the machine 1320 may have a cooking or heating element 1332 such that the vending-style machine prepares cooked, ready-to-eat pizza without requiring an associate, worker, or attendant to process the incoming food orders. As noted above, whether or not a particular food preparation facility 1304 is capable of heating or cooking the food orders may be tracked in the database 1310, such that customers are able to know whether they will be able to get a baked pizza.

Accordingly, the control circuit 1322 of the automated pizza preparation machine 1320 is typically in communication with the control circuit 1306 (which coordinates with multiple food preparation facilities 1304 of the pizza ordering system 1300) to update the database 1310. By one approach, the pizza preparation machine 1320 monitors ingredient levels, such as via sensors 1324, to help determine availability of ingredients and other system capacities such as the heating element 1332. In one illustrative approach, these ingredient levels and machine capabilities are tracked in a local database 1326 that is used to update the system database 1310 in a number of manners. Upon detection that a particular ingredient is below a certain level, via the sensors 1324, the device control circuit 1322 may update the database 1326 or notify the system control circuit 1306 that updates and maintains the database 1310 of available ingredients and capabilities for each of the food preparation facilities 1304 in the system 1300. By another approach, the local database 1326 of the automated pizza preparation machine 1320 may track the original amount of ingredient level in the machine 1320 and then tracks the amount of ingredients dispensed to track the remaining level of product or ingredient so that the database 1310 may be maintained. The information from the local database 1326 may be regularly or routinely shared with the system control circuit so that the database 13210 may be updated.

As noted above, the systems and methods herein maintain a database of food preparation facilities (including retail facilities with workers therein and automated pizza preparation machines that may be independent or incorporated into a retail facility) and their available ingredients and capabilities (including the ability to prepare a cooked or baked pizza at a certain time). In this manner, the customer accessing the user interface 102, 1302 knows what particular ingredients are available (not just the menu items that are available), thereby permitting the user to customer the details of their order (i.e., ingredients and preparation aspects). This also provides the user with a level of confidence that their requested customizations will be properly executed.

As an updated database facilitates the ingredient level customization, the maintenance of the database is designed to be quick and incorporated into the process in a regular, systemic manner. While the database may be maintained in a number of manner, a few illustrative options are noted herein. By one approach, the control circuit 106, 1306 may multicast an inquiry regarding the ingredient levels and device capabilities to food preparation facilities, such as for example, to the control circuit 1322 or the associate interface units 104. Accordingly, the control circuit 106, 1306 may communicate with a number of different food preparation facilities concurrently to update the database(s) of ingredient availability and preparation capabilities. In turn, these the devices at the food preparation facilities respond to the control circuit 106, 1306 with information regarding the associated facilities' availabilities and capabilities such that the control circuit 106, 1306 may update the databases 110, 1310 or the devices may update the databases 110, 1310 directly. The multicast inquiry may be a regularly occurring event or may be prompted by a particular volume of orders, among other triggers. By another approach, the food preparation facilities (such as via control circuits or user interface units in connection therewith) may be configured to notify the control circuit 106, 1306 regarding ingredient levels or capabilities or update the database(s) 110, 1310 directly, such as, for example, when a particular ingredient threshold has been reached or at particular time intervals.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A food order processing system comprising:
   an electronic user interface unit configured to receive a food order, a user-selected retrieval time, and a user-selected food preparation facility from a user;
   a database of a plurality of food preparation facilities and capabilities associated with the plurality of food preparation facilities;
   one or more sensors configured to detect ingredient levels associated with at least one of the plurality of food preparation facilities, wherein multiple food preparation facilities have the one or more sensors disposed therein;
   one or more facility electronic interface units disposed at the plurality of food preparation facilities, the facility electronic interface units configured to display details of multiple submitted food orders to associates at the one or more of the plurality of food preparation facilities; and
   a central computer coupled to the database and in communication with the electronic user interface unit, the one or more sensors, and the one or more facility electronic interface units, the central computer configured to:
   receive ingredient level information from the one or more sensors configured to detect ingredient levels, upon detection of a particular ingredient below a threshold level;
   maintain in the database the capabilities associated with the plurality of food preparation facilities including available ingredients and food preparation selections available for selection by the user;
   updating an ingredient level in the database based on information received from the one or more sensors regarding the detected ingredient levels associated with a particular one of the plurality of food preparation facilities, such that the database is updated with real-time ingredient levels from multiple food preparation facilities;
   receive the user-selected retrieval time and the user-selected food preparation facility for the food order received at the user interface unit;
   present, based upon information from the database, the available ingredients and food preparation selections to the user based on the received user-selected retrieval time and the user-selected food preparation facility;
   receive ingredient and food preparation selections from the user for the food order;
   notify the user-selected food preparation facility of the food order, retrieval time, and the ingredient and food preparation selections; and
   periodically send multicast inquiries to the facility electronic interface units at the multiple food preparation facilities from the control regarding at least one of facility capabilities and ingredient levels and update the database in light of received responses.

2. The system of claim 1 wherein the central computer system is further configured to modify the user-selected retrieval time of the food order if the selected food preparation facility cannot accommodate the food order having the received ingredient and food preparation selections made by the user.

3. The system of claim 1 wherein the central computer system is further configured to notify the user that the selected food preparation facility cannot accommodate the user-selected retrieval time of the food order having the received ingredient and food preparation selections made by the user.

4. The system of claim 1 wherein the central computer system is further configured to present the user with suggested food preparation facilities based on a user location.

5. The system of claim 1 wherein the central computer system is further configured to notify the user of a status of the food order.

6. The system of claim 1 wherein the plurality of food preparation facilities are configured to receive payments for food orders via the facility electronic interface units.

7. The system of claim 1 wherein the database is updated with the currently available ingredients and food preparation selections substantially in real-time.

8. The system of claim 1 wherein the food preparation facilities are configured to receive payment for remotely-placed food orders.

9. The system of claim 8 wherein individual ones of the multiple food preparation facilities are configured to prepare uncooked and cooked pizzas for retrieval by the users and the food preparation selections include at least one of: a number of pizzas, pizza size, pizza crust type, and a cooked status.

10. The system of claim 8 wherein the selected food preparation facility is configured to prepare the received-food order for retrieval at the selected food preparation facility before the selected retrieval time.

11. The system of claim 8 wherein the selected food preparation facility is instructed, via one of the facility electronic interface units, to route a previously prepared food order for purchase or consumption to individuals other than the user at a pre-determined time after the user-selected retrieval time.

12. The system of claim 1 wherein the user interface unit is at least one of: a store kiosk, a mobile computer, or a desktop computer.

13. The system of claim 1 wherein individual ones of the multiple food preparation facilities are configured to prepare uncooked and cooked pizza for retrieval by the users and the system further comprising an automated pizza preparation machine.

14. The system of claim 1 wherein the one or more sensors are further configured to detect capabilities of the at least one of the plurality of food preparation facilities and the central computer is further configured to update the database in light of the detected capabilities.

15. The system of claim 1 wherein at least one of the facility electronic interface units is further configured to receive information regarding ingredient availability and the capabilities of the food preparation facility from an associate.

16. The system of claim 1 wherein at least one of the facility electronic interface units is further configured to assist associates with managing received food orders by visually highlighting orders for preparation according to requested retrieval time.

17. The system of claim 16 wherein at least one of the facility electronic interface units is further configured to assist associates with managing received food orders by permitting the associates to input order status, which may be communicated to the user, via the control circuit.

18. A computer implemented method comprising:
presenting to a user, via an electronic user device, an opportunity to initiate a food order;
receiving, from the electronic user device, a retrieval time and a selected food preparation facility for the food order;
maintaining, in a database, capabilities associated with a plurality of food preparation facilities;
receiving, at a control circuit, ingredient level information, upon detection of a particular ingredient below a predetermine threshold, from one or more sensors associated with the plurality of food preparation facilities and updating the database in light of the received ingredient level information from multiple food preparation facilities, such that the database is updated with real-time ingredient levels from the multiple food preparation facilities;
presenting available food items for customization including ingredients and food preparation offerings associated with the selected food preparation facility based on information in the database;
receiving, via the electronic user device, the food order with at least one customized food item;
determining whether the selected food preparation facility can accommodate the food order and the retrieval time;
notifying the selected food preparation facility of the retrieval time and the food order with the customized food item;
receiving, at one of the plurality of food preparation facilities, details of multiple food orders and displaying details of the multiple food orders, via one or more facility electronic interface units disposed at the one of the plurality of preparation facilities, for preparation thereof;
periodically sending multicast inquires to the facility electronic interface units at the multiple food preparation facilities from the control circuit regarding at least one of facility capabilities and ingredient levels and updating the database in light of received responses; and
receiving payment for the food order when the user retrieves the food order at the selected food preparation facility.

19. The method of claim 18 further comprising, for a particular selected food preparation facility, updating, in the database, availability of the ingredients and food preparation offerings presented to the user that are used for customizing the food order.

20. The method of claim 18 further comprising notifying the selected food preparation facility of a user's estimated arrival time using a global positioning system-enabled (GPS-enabled) device carried by the user.

21. The method of claim 18 further comprising modifying the retrieval time of the food order in response to at least one of the following: circumstances at the selected food preparation facility, receipt of additional food orders, and size of the food order.

22. The method of claim 18 further comprising preparing the food order at the selected food preparation facility before the retrieval time.

23. The method of claim 18 further comprising providing the food order for purchase or consumption to individuals other than the user at a pre-determined time after the retrieval time.

24. The method of claim 18 further comprising detecting capabilities of the associated at least one of the plurality of food preparation facilities and updating the database in light of the detected capabilities.

* * * * *